United States Patent [19]

Flament

[11] 4,166,869

[45] Sep. 4, 1979

[54] USE OF CERTAIN ACYL-PYRIMIDINES AS FLAVOURING AGENTS

[75] Inventor: Ivon Flament, Petit-Lancy, Switzerland

[73] Assignee: Firmenich, S.A., Geneva, Switzerland

[21] Appl. No.: 867,367

[22] Filed: Jan. 6, 1978

[30] Foreign Application Priority Data

Jan. 10, 1977 [CH] Switzerland .......................... 227/77

[51] Int. Cl.$^2$ ...................... A23L 1/226; A23L 1/231; A23L 1/234
[52] U.S. Cl. .................................. 426/537; 544/335
[58] Field of Search ........................ 426/537; 544/335

[56] References Cited

U.S. PATENT DOCUMENTS

| | | | |
|---|---|---|---|
| 3,764,601 | 10/1973 | Evers et al. | 426/537 X |
| 3,843,804 | 10/1974 | Evers et al. | 426/537 |
| 3,857,972 | 12/1974 | Evers et al. | 426/537 X |

Primary Examiner—Joseph M. Golian
Attorney, Agent, or Firm—Scully, Scott, Murphy & Presser

[57] ABSTRACT

Use of certain acyl-pyrimidine derivatives as flavouring and taste-modifying agents in the aromatization of foodstuffs in general and imitation flavours for foodstuffs, beverages, animal feeds, pharmaceutical preparations and tobacco products.

6 Claims, No Drawings

USE OF CERTAIN ACYL-PYRIMIDINES AS FLAVOURING AGENTS

SUMMARY OF THE INVENTION

The compounds to which the present invention relates belong to the class of acyl-pyrimidine derivatives having the formula

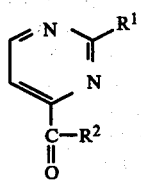

wherein symbol R' represents a hydrogen atom or a methyl radical and R² stands for a lower alkyl radical containing from 1 to 6 carbon atoms.

The compounds of formula (I) possess interesting organoleptic properties and consequently may be conveniently used in the flavour industry.

BACKGROUND OF THE INVENTION

In the course of the last decade particularly great attention has been devoted by various research groups to the study of the flavour properties of heterocyclic compounds, viz. nitrogen containing heterocyclic compounds. Various pyrazines have been shown in the literature to have flavour implications and have been considered essential ingredients for the reconstitution of flavour compositions of different nature [see e.g.: Fenaroli's Handbook of Flavor Ingredients, CRC Press, Inc., Cleveland (1975), vol. II, p. 692 and ff.; United Kingdom Pat. Nos. 1,156,472, 1,156,475 and 1,156,484].

Certain nitrogen containing heterocyclic derivatives belonging to the class of pyridines, pyrroles as well as thiazoles have also been described as possessing useful gustative properties [see e.g.: United Kingdom Pat. Nos. 1,156,483, 1,156,482 and 1,156,485]. Up to now, however, no suggestion has been formulated as to the possibility of using pyrimidic compounds as flavouring ingredients.

THE INVENTION

It has now unexpectedly been found that the flavour and the taste of foodstuffs in general, beverages, animal feeds, pharmaceutical preparations and tobacco products can be altered by adding thereto a small but effective amount of at least one compound of formula (I).

A particularly preferred class of the said compounds include

| | |
|---|---|
| 4-acetyl-pyrimidine | |
| 2-methyl-4-acetyl-pyrimidine | n.c. |
| 4-propionyl-pyrimidine | |
| 2-methyl-4-propionyl-pyrimidine | n.c. |
| 4-butyryl-pyrimidine | n.c. |
| 2-methyl-4-butyryl-pyrimidine | n.c. |
| 4-isobutyryl-pyrimidine | n.c. |
| 2-methyl-4-isobutyryl-pyrimidine | n.c. |
| 4-valeryl-pyrimidine | n.c. |
| 2-methyl-4-valeryl-pyrimidine | n.c. |
| 4-isovaleryl-pyrimidine and | n.c. |
| 2-methyl-4-isovaleryl-pyrimidine | n.c. |

Most of the above cited compounds are new and are defined by the abbreviation "n.c."

The new compounds cited above include those compounds of particular interests defined by the following formula (I')

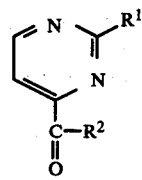

wherein either symbol R' represents a hydrogen atom and R² stands for an isobutyl radical, or symbol R' represents a methyl radical and R² stands for a methyl, an ethyl or an isobutyl radical.

One of the objects of the invention relates to a process for enhancing, improving or modifying the flavour properties of foodstuffs, beverages, animal feeds, pharmaceutical preparations and tobacco products, which process comprises the step of adding to said materials a small but effective amount of at least one of the compounds of formula (I). This invention relates further to a flavour composition which comprises having added thereto at least one of the compounds of formula (I).

More particularly, the invention provides a process for modifying the organoleptic properties of meat, meat imitating or meat containing consumable materials which process comprises adding to said materials at least one of the compounds of formula (I).

PREFERRED EMBODIMENTS OF THE INVENTION

In their pure state the compounds of formula (I) develop gustative notes of various type, such as e.g. animal, grilled, roasted and fatty flavour notes. Their flavour character, sweetish and caramel-like, is reminiscent of the taste developed by meat. Typically, the compounds of formula (I) find a very useful application in the manufacture of flavour compositions destined to the aromatization of meat, meat imitating or meat substituting edible materials. However, it has to be understood that owing to their gustative properties the pyrimidines of formula (I) find a broad spectrum of utility and they can be employed in a wide range of materials such as e.g. coffee, chocolate, dairy products, yoghurts, confectionary and bakery materials.

Compounds (I) find also a useful application in the aromatization of tobacco and tobacco substitute products.

The proportions at which the said compounds can achieve interesting gustative effects vary within wide limits. Preferentially, these proportions are of from about 0.02 to about 20 ppm (parts per million) by weight based on the total weight of the material into which they are incorporated. These values, however, should not be interpreted restrictively and it should be understood by those skilled in the art that concentrations lower or higher than those indicated above may be used whenever it is desired to achieve special effects. It is moreover well known in the art that the concentrations of a given flavourant depend on the nature of the specific material it is desired to aromatize and on the nature of the coingredients in a given composition. Pyrimidines (I) can in fact be used as such, either by effecting a direct addition of them in their pure state or, more frequently, by adding them in the form of a solution in a current edible solvent, such as ethanol, dipropyleneglycol or triacetine, or in admixture with other flavour ingredients in the form of a flavour composition.

Pyrimidines (I) can be prepared by using conventional processes. The processes are illustrated in details in the following experimental section wherein temperatures are indicated in degrees centigrade and the abbreviations have the meaning common in the art.

4-Acetyl-pyrimidine, 4-propionyl-pyrimidine and 4-isovaleryl-pyrimidine were prepared by a process in accordance with the following reaction scheme I.

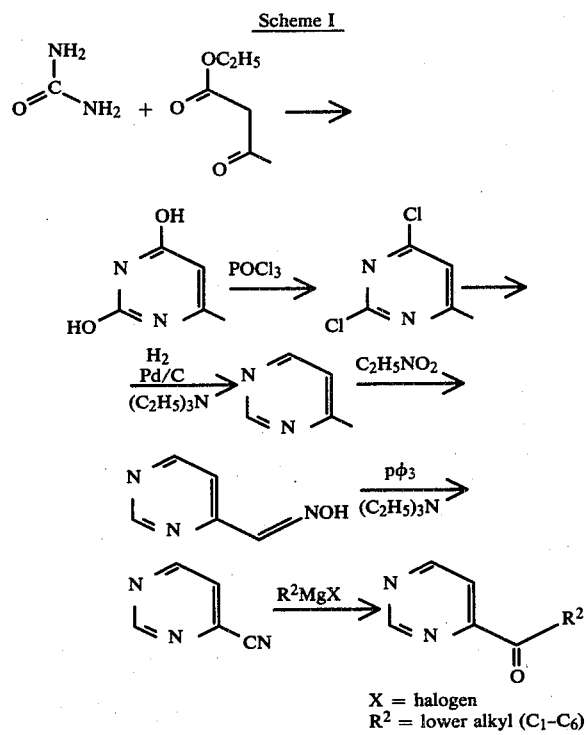

X = halogen
R$^2$ = lower alkyl (C$_1$-C$_6$)

a. 2,4-Dihydroxy-6-methyl-pyrimidine

The title compound was prepared in accordance with the method described in Org. Synth. Coll. vol. 2, 422 (1969), starting from ethyl-acetoacetate and urea.

b. 2,4-Dichloro-6-methyl-pyrimidine 45 g (0.36 M) of 2,4-dihydroxy-6-methyl-pyrimidine have been treated with phosphorous oxychloride in the presence of diethylaniline. After having been refluxed during 3 hours the reaction mixture was cooled and the excess of phosphorous oxychloride was decomposed over ice, then the mixture was neutralized with NaOH, saturated with a NaCl solution and extracted with ether. By separation and evaporation of the ethereal extracts there was obtained a residue which was distilled to yield 57 g of the title compound at B.p. 99°/11 Torr.

c. 4-Methyl-pyrimidine

The product obtained according to paragraph b. above was dissolved in 500 ml of diethylether containing an equivalent amount of triethylamine and 5 g of palladium over charcoal (5%) and the solution was stirred during 5½ hrs in an atmosphere of hydrogen. After filtration, evaporation and distillation there was obtained the title compound in a yield of about 80%. B.p. 35°/12 Torr.

d. 4-Formyl-pyrimidine-oxime

4-Methyl-pyrimidine (0.1 M) was added to 100 ml of ethanol containing 3.5 g (0.1 M) of HCl. While keeping the reaction mixture at 5° there was added over 60 minutes a solution of 9 g (0.12 M) of ethyl nitrite in 60 ml of ethyl alcohol, whereupon the whole was kept under stirring for 1 hour at room temperature. The thus formed 4-formyl-pyrimidine-oxime hydrochloride was separated by filtration, dissolved in water and the aqueous solution neutralized by adding Na$_2$CO$_3$. The title compound was finally obtained by filtration and drying. M.p. 154°–155°. Yield 71%.

e. 4-Cyano-pyrimidine

A solution of 0.01 M of the oxime prepared according to paragraph d. above, 0.012 M of triphenylphosphine, 0.01 M of carbon tetrachloride and 0.01 M of triethylamine in 50 ml of 1,2-dichloroethane was heated for 2 hours at 60°. The volatile components were taken off and the residue was extracted with 4 fractions of 100 ml of petrolether (B.p. 30°–50°). After evaporation and distillation of the organic extracts 4-cyano-pyrimidine was obtained in a 61% yield.

f. 4-Acetyl-pyrimidine

A solution of 0.05 M of methyl bromide in 15 ml of ether was added to 0.04 at.gr. of magnesium turnings in 15 ml of dry ether and the suspension obtained was refluxed until complete solution of the magnesium present (30 min). The solution was then cooled to −15° and a solution of 0.025 M of 4-cyano-pyrimidine in 20 ml of ether was added thereto. 50 ml of ether was further added to the reaction mixture and stirring was carried out for 30 min. at −10°, then for 30 min. at room temperature.

The mixture was then poured onto 100 g of ice, acidified with conc. H$_2$SO$_4$ and stirred 15 min. at room temperature. After neutralisation with solid sodium carbonate, continuous extraction with ether and evaporation of the ethereal extracts there was obtained a residue which was purified by preparative gas chromatography by using a CARBOWAX column 20M. 4-Acetyl-pyrimidine was obtained in 53% yield.

MS:m/e (%):

|     | 0    | 1    | 2    | 3    | 4    | 5   | 6   | 7   | 8   | 9    |
|-----|------|------|------|------|------|-----|-----|-----|-----|------|
| 20  | —    | —    | —    | —    | —    | —   | 7.1 | 4.9 | —   | 2.6  |
| 30  | —    | —    | —    | —    | —    | —   | —   | 1.4 | 2.5 | 5.9  |
| 40  | 2.7  | 7.2  | 6.7  | 100. | —    | —   | —   | —   | —   | —    |
| 50  | 1.7  | 11.1 | 50.4 | 46.3 | 1.8  | 4.1 | 1.8 | 3.2 | —   | —    |
| 60  | —    | —    | —    | —    | —    | —   | 1.6 | 4.9 | 2.1 | 3.1  |
| 70  | 1.3  | 1.9  | —    | —    | —    | —   | —   | —   | —   | 26.2 |
| 80  | 64.8 | 10.1 | 2.8  | 2.0  | —    | —   | —   | —   | —   | —    |
| 90  | —    | —    | —    | 2.4  | 35.4 | 4.0 | —   | —   | —   | —    |
| 100 | —    | —    | —    | —    | —    | —   | —   | 2.5 | 1.4 | 1.8  |
| 110 | —    | —    | —    | —    | —    | —   | —   | —   | —   | —    |
| 120 | —    | —    | 47.5 | 3.0  |      |     |     |     |     |      | f′. 4-Propionyl-pyrimidine

By replacing in the hereinabove given procedure methyl bromide by ethyl bromide, the title compound was obtained in 11% yield.

MS:m/e (%)

|     | 0    | 1    | 2    | 3    | 4    | 5    | 6    | 7    | 8    | 9    |
|-----|------|------|------|------|------|------|------|------|------|------|
| 20  | —    | —    | —    | —    | —    | —    | 13.7 | 27.7 | 36.3 | 97.5 |
| 30  | 1.4  | —    | —    | —    | —    | —    | —    | 1.1  | 1.2  | 3.2  |
| 40  | .8   | 1.6  | 1.4  | 1.8  | —    | —    | —    | —    | —    | —    |
| 50  | 1.2  | 11.0 | 73.2 | 43.9 | 2.7  | 4.0  | 9.8  | 100. | 2.6  | —    |
| 60  | —    | —    | —    | —    | —    | —    | —    | —    | —    | 1.2  |
| 70  | —    | —    | —    | —    | —    | —    | —    | —    | —    | 51.2 |
| 80  | 97.8 | 26.5 | 1.8  | —    | —    | —    | —    | —    | —    | —    |
| 90  | —    | —    | —    | 1.8  | 19.6 | 1.5  | —    | —    | —    | —    |
| 100 | —    | —    | —    | —    | —    | —    | 1.6  | 27.8 | 75.2 | 4.7  |
| 110 | —    | —    | —    | —    | —    | —    | —    | —    | —    | —    |
| 120 | —    | 1.6  | —    | —    | —    | —    | —    | —    | —    | —    |
| 130 | —    | —    | —    | —    | —    | 13.5 | 41.0 | 3.4  |      |      | f''. 4-Isovaleryl-pyrimidine

By replacing in the above given procedure f. methyl bromide by isobutyl bromide, the title compound was obtained in 18% yield.

MS:m/e (%)

|     | 0    | 1    | 2    | 3    | 4    | 5    | 6    | 7    | 8    | 9    |
|-----|------|------|------|------|------|------|------|------|------|------|
| 20  | —    | —    | —    | —    | —    | —    | 4.1  | 16.3 | —    | 21.5 |
| 30  | —    | —    | —    | —    | —    | —    | —    | —    | 1.3  | 15.7 |
| 40  | 2.5  | 89.9 | 6.0  | 18.5 | —    | —    | —    | —    | —    | —    |
| 50  | —    | 4.5  | 28.6 | 21.2 | 2.4  | 5.8  | 3.4  | 52.3 | 2.4  | —    |
| 60  | —    | —    | —    | —    | —    | 1.5  | 1.5  | 3.9  | 1.3  | 13.1 |
| 70  | 1.1  | 1.5  | —    | —    | —    | —    | —    | 2.5  | 1.5  | 32.3 |
| 80  | 100. | 17.6 | 2.3  | 2.6  | 1.2  | 14.4 | 1.3  | —    | —    | —    |
| 90  | —    | 3.6  | 1.6  | 3.1  | 16.1 | 2.5  | —    | —    | —    | —    |
| 100 | —    | —    | —    | —    | —    | 1.9  | 1.5  | 19.5 | 41.8 | 4.7  |
| 110 | 1.9  | —    | —    | —    | —    | —    | —    | —    | —    | 1.6  |
| 120 | 1.1  | 11.3 | 7.4  | 3.4  | —    | —    | —    | —    | —    | —    |
| 130 | —    | —    | —    | 2.7  | 2.0  | 2.6  | 4.7  | 2.1  | —    | —    |
| 140 | —    | —    | —    | —    | —    | —    | —    | —    | —    | 18.3 |
| 150 | 2.4  | —    | —    | —    | —    | —    | —    | —    | —    | —    |
| 160 | —    | —    | —    | —    | 17.5 | 2.5  |      |      |      |      |

2-Methyl-4-acetyl-pyrimidine, 2-methyl-4-propionyl-pyrimidine and 2-methyl-4-isovaleryl-pyrimidine were prepared by a process in accordance with the following reaction scheme II.

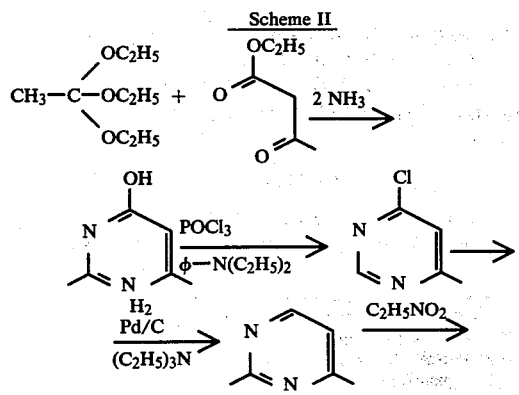

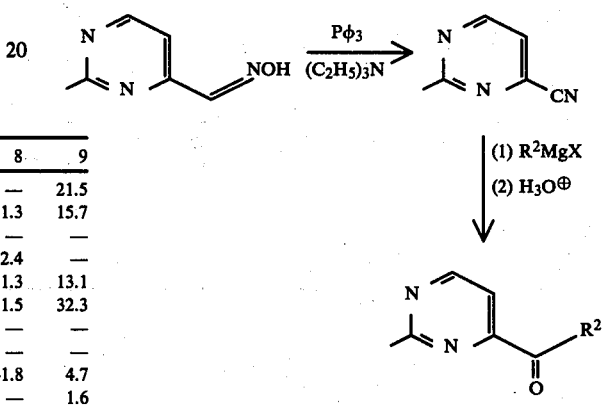

Yield
$R^2 = CH_3$ 73%
 $= C_2H_5$ 16%
 $= iC_4H_9$ 34% a. 4-Hydroxy-2,6-dimethyl-pyrimidine

A solution of 405 g (2.5 M) of ethyl ortho-acetate and 295 g (2.5 M) of ethyl acetoacetate in 500 ml of methylalcohol was refluxed for 15 min. During reflux a constant flow of gaseous ammonia was bubbled through the solution. After evaporation of the solvent, the formed pyrimidine was precipitated by adding 500 ml of ether. 190 g of the title compound was thus obtained (yield 61.3%). The further steps to convert the obtained 4-hydroxy-2,6-dimethyl-pyrimidine into the desired acyl pyrimidine were carried out in accordance with the procedure described in steps b. to f. given above.

2-Methyl-4-acetyl-pyrimidine

MS:m/e (%): 27 (3.1), 29 (3.6), 38 (2.6), 39 (5.1), 40 (5.1), 41 (6.7), 42 (82.0), 43 (78.5), 51 (3.1), 52 (19.5), 53 (30.8), 66 (20.5), 67 (15.9), 93 (72.3), 94 (100), 95 (6.1), 108 (33.3), 136 (95.9), 137 (7.2).

NMR: 2.69 and 2.80 (6H, 2s), 7.65 and 8.85 (2H, d, J=5 cps) δ ppm;

IR: 3050, 3020, 2980, 2940, 1715, 1570, 1435, 1395, 1363, 1300, 1272, 1170, 1125, 1097, 1050, 996, 980, 960 and 852 cm$^{-1}$.

2-Methyl-4-propionyl-pyrimidine

MS:m/e (%):

|     | 0 | 1 | 2 | 3 | 4 | 5 | 6 | 7 | 8 | 9 |
|---|---|---|---|---|---|---|---|---|---|---|
| 20 | — | — | — | — | — | — | 5.9 | 18.6 | — | 54.8 |
| 30 | — | — | — | — | — | — | — | 1.5 | 2.7 | 7.3 |
| 40 | 4.7 | 10.0 | 72.7 | 3.7 | — | — | — | — | — | — |
| 50 | — | 3.8 | 21.6 | 25.0 | 2.9 | 2.8 | 6.7 | 56.2 | 2.1 | — |
| 60 | — | — | — | — | 1.7 | 2.8 | 18.2 | 7.2 | 2.1 | 3.8 |
| 70 | — | — | — | — | — | — | — | — | 1.7 | 2.4 |
| 80 | 2.9 | 2.7 | 1.8 | — | — | — | — | — | — | — |
| 90 | — | 1.3 | 1.5 | 62.1 | 100. | 20.8 | 2.2 | — | — | — |
| 100 | — | — | — | — | — | — | — | 1.8 | 13.5 | 3.3 |
| 110 | — | — | — | — | — | — | — | — | — | — |
| 120 | 2.2 | 24.1 | 63.3 | 5.6 | — | — | — | — | — | — |
| 130 | — | — | — | 1.7 | — | — | — | — | — | — |
| 140 | — | — | — | — | — | — | — | — | 9.4 | — |
| 150 | 36.5 | 2.9 | | | | | | | | |

2-Methyl-4-isovaleryl-pyrimidine

MS:m/e (%):

|     | 0 | 1 | 2 | 3 | 4 | 5 | 6 | 7 | 8 | 9 |
|---|---|---|---|---|---|---|---|---|---|---|
| 20 | — | — | — | — | — | — | — | 4.4 | — | 7.5 |
| 30 | — | — | — | — | — | — | — | — | — | 5.6 |
| 40 | 1.4 | 17.2 | 32.2 | 6.3 | 6.7 | — | — | — | — | — |
| 50 | — | — | 6.1 | 8.2 | — | — | — | 26.5 | — | — |
| 60 | — | — | — | — | — | 1.5 | 4.5 | 2.6 | — | 3.7 |
| 70 | — | — | — | — | — | — | — | — | — | — |
| 80 | — | — | — | — | — | 1.9 | — | — | — | — |
| 90 | — | — | — | 30.0 | 100. | 10.3 | — | — | — | — |
| 100 | — | — | — | — | — | — | — | — | 13.1 | 1.9 |
| 110 | — | — | — | — | — | — | — | — | — | — |
| 120 | — | 2.6 | 15.8 | 1.9 | — | — | — | — | — | — |
| 130 | — | — | — | — | 4.7 | 3.8 | 2.3 | — | — | — |
| 140 | — | — | — | — | — | — | — | — | — | 1.4 |
| 150 | 2.3 | — | — | — | — | — | — | — | — | — |
| 160 | — | — | — | 16.5 | 2.7 | — | — | — | — | — |
| 170 | — | — | — | — | — | — | — | — | 10.9 | 2.9 |
| 180 | | | | | | | | | | |

2-Methyl-4-acetyl-pyrimidine can also be prepared in accordance with the procedure illustrated by the following reaction scheme.

Scheme III

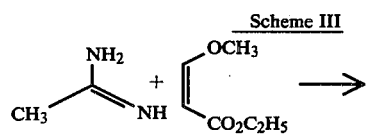

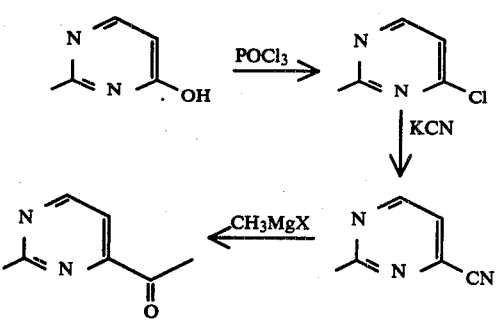

X = halogen

The invention is better illustrated by but not limited to the following examples.

EXAMPLE 1

A comparative flavour evaluation was carried out by tasting in crystal spring water the following compounds in the concentrations indicated:

| Compound | dosage (ppm) | evaluation |
|---|---|---|
| 1. 2-Methyl-4-acetyl-pyrimidine | 0.5 | roasted, animal, meat-like, sweetish, caramel, nut |
| 2. 3-acetyl-pyridine | 2.5 | less meat-like than 1., hazelnut, roasted, cereal-like, less "body" than 1. |
| 3. 2-acetyl-pyrazine | 1.0 | animal, less meaty and roasted than 1. Fatty |
| 4. 5-methyl-quinoxaline | 2.5 | less meaty and animal than 1. Hazelnut, roasted, slightly green |

The above given comparison test shows the basic difference inasmuch as the flavour characters are concerned between 2-methyl-4-acetyl-pyrimidine and compounds 2 to 4 known in the art for promoting meat-like flavour notes.

EXAMPLE 2

A reconstituted beef broth was prepared by mixing together the following ingredients (parts by weight):

| | |
|---|---|
| Commercial beef extract | 10 |
| Monosodium glutamate | 1 |
| 50:50 Mixture of sodium inositate: sodium guanilate | 0.0005 |

-continued

|  |  |
|---|---|
| Sodium chloride | 8 |
| Lactic acid | 0.5 |
| Water | 980.495 |
| Total | 1000.000 |

The broth thus prepared was divided into 3 portions of equal volume. Two of these portions were aromatized with 0.15, respectively 0.30 ppm of 2-methyl-4-acetyl-pyrimidine and the thus flavoured foodstuffs were subjected to the evaluation by a panel of flavour experts who expressed their judgement as follows:

a. non-aromatized broth: bland taste, meaty character, protein, vegetable taste b. aromatized broth (0.15 ppm): the meaty taste was more marked than that of a.

c. aromatized broth (0.30 ppm): strong roasted and animal character.

EXAMPLE 3

An artificial beef broth was prepared by mixing together the following ingredients (parts by weight):

|  |  |
|---|---|
| Vegetable fat | 22.00 |
| Tomato concentrate (40%) | 11.50 |
| Sodium chloride | 7.25 |
| Monosodium glutamate | 9.00 |
| Hydrolized plant protein | 11.00 |
| Caramel color | 1.20 |
| Ground white pepper | 0.15 |
| Onion powder | 0.15 |
| Sugar | 4.75 |
| Wheat floor | 19.50 |
| Corn starch | 13.50 |
| Total | 80.00 |

130 g of the thus obtained mixture were added under stirring to 1 lt of hot water and boiled for 2 minutes. The resulting gravy mix was divided into 3 portions of equal volume. Two of these portions were aromatized with 0.30, respectively 0.50 ppm of 2-methyl-4-acetyl-pyrimidine and the obtained flavoured foodstuffs were tasted by comparison with the unflavoured broth. The panel of flavour experts expressed their view on the flavour quality of the submitted foodstuffs as follows:

a. non-aromatized broth: sweet, fruity, typical protein hydrolysate taste.

b. aromatized broth (0.30 ppm): more pronounced meaty character, roasted, slightly caramel c. aromatized broth (0.50 ppm): more roasted than a.; nut character.

EXAMPLE 4

A praline chocolate centre filling was prepared by mixing the following ingredients (parts per weight):

|  |  |
|---|---|
| Natural praline | 100.0 |
| Vegetable fat (M.p. 34° C.) | 40.0 |
| Slum milk powder | 20.0 |
| Icing sugar | 40.0 |
| Lecithin | 1.0 |
| Antioxydant | 0.1 |
| Total | 201.1 |

The foodstuff thus prepared was divided into 3 portions of equal volume. Two of these portions were aromatized with 0.30, respectively 0.50 ppm of 2-methyl-4-acetyl-pyrimidine and the thus flavoured foodstuffs were evaluated by a group of flavour experts who declared:

a. non-aromatized foodstuff: sweet, bland roasted hazelnut character b. aromatized foodstuff (0.30 ppm): typical character of nut c. aromatized foodstuff (0.50 ppm): more roasted than a., nut character

EXAMPLE 5

Coffee aromatization 3.2 g of commercial instant coffee powder were dissolved in ca. 240 ml of boiling water and the obtained drink was divided into two fractions of equal volume. One of them was flavoured with 2-methyl-4-acetyl-pyrimidine at a concentration of 0.075 ppm and the thus obtained flavoured drink was subjected to an organoleptic evaluation by comparison with the unflavoured coffee drink. The taste and aroma of the flavoured drink were found to possess a more pronounced roasted character as well as a more marked nut aroma.

EXAMPLE 6

Tobacco aromatization 0.3 g of a 1°/oo solution of 2-methyl-4-acetyl-pyrimidine in 95% ethanol were sprayed onto 100 g of a mixture of tobacco of "american blend" type. The tobacco thus flavoured was used to manufacture "test" cigarettes, the smoke of which was then subjected to organoleptic evaluation by comparison with non-flavoured cigarettes ("control"). The tobacco used to manufacture the control cigarettes was preliminary treated with 95% ethanol. The panel of experts declared that the taste of the test cigarettes possessed more body and more defined flavour character reminiscent of the taste of hazelnuts.

Examples 7–10

An evaluation of the flavour properties of various acyl-pyrimidines was carried out in crystal spring water. The obtained results are indicated hereinbelow:

a. 4-acetyl-pyrimidine: sweet, slightly fruity, caramel b. 4-propionyl-pyrimidine: fruity, ethereal, slightly flowery c. 2-methyl-4-propionyl-pyrimidine: slightly fruity d. 2-methyl-4-isovaleryl-pyrimidine: burnt, sweet, cocoa character

What I claim is:

1. Process for enhancing or improving animal, grilled, roasted and fatty flavour notes in foodstuffs, beverages and animal feeds which comprises the step of adding thereto from about 0.02 to about 20 parts per million by weight, based on the total weight of the said materials, of at least one of the compounds of formula

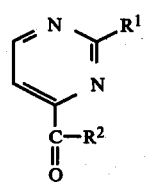

wherein symbol $R^1$ represents a hydrogen atom or a methyl radical and $R^2$ stands for a lower alkyl radical containing from 1 to 6 carbon atoms.

2. The process of claim 1 wherein the foodstuff is meat, a meat imitating or a meat containing consumable material.

3. The process according to claim 1 wherein the compound is 2-methyl-4-acetyl-pyrimidine.

4. The process according to claim 1 wherein the compound is 2-methyl-4-propionyl-pyrimidine.

5. The process according to claim 1 wherein the compound is 4-isovaleryl-pyrimidine.

6. The process according to claim 1 wherein the compound is 2-methyl-4-isovaleryl-pyrimidine.

* * * * *

UNITED STATES PATENT AND TRADEMARK OFFICE
CERTIFICATE OF CORRECTION

PATENT NO. : 4,166,869
DATED : September 4, 1979
INVENTOR(S) : Ivon Flament

It is certified that error appears in the above-identified patent and that said Letters Patent are hereby corrected as shown below:

Column 7, line 28:  140 — — — — — — — — 9.4 — should be

140 — — — — — — — — — 9.4

Column 7, line 54:  150  2.3 — — — — — — — — — should be 150  2.8 — — — — — — — — —

Signed and Sealed this

*Eighth* Day of *January 1980*

[SEAL]

*Attest:*

SIDNEY A. DIAMOND

*Attesting Officer*             *Commissioner of Patents and Trademarks*